United States Patent
Shahine

(10) Patent No.: US 9,816,976 B2
(45) Date of Patent: Nov. 14, 2017

(54) SYSTEM AND METHOD OF DETECTING ATMOSTPHERIC TRACE GAS CONCENTRATIONS IN A CELL

(71) Applicant: Mohamad Haidar Shahine, Ellicott City, MD (US)

(72) Inventor: Mohamad Haidar Shahine, Ellicott City, MD (US)

(*) Notice: Subject to any disclaimer, the term of this patent is extended or adjusted under 35 U.S.C. 154(b) by 64 days.

(21) Appl. No.: 14/860,712

(22) Filed: Sep. 22, 2015

(65) Prior Publication Data
US 2016/0084760 A1    Mar. 24, 2016

Related U.S. Application Data

(60) Provisional application No. 62/054,368, filed on Sep. 23, 2014.

(51) Int. Cl.
| | |
|---|---|
| *G01N 21/39* | (2006.01) |
| *G01N 33/00* | (2006.01) |
| *G01J 3/433* | (2006.01) |
| G01N 21/3504 | (2014.01) |
| G01N 21/17 | (2006.01) |

(52) U.S. Cl.
CPC ............ *G01N 33/004* (2013.01); *G01J 3/433* (2013.01); *G01N 21/39* (2013.01); *G01N 33/007* (2013.01); *G01N 21/3504* (2013.01); *G01N 2021/1795* (2013.01); *G01N 2201/12* (2013.01)

(58) Field of Classification Search
CPC .. G01N 21/39; G01N 21/3504; G01N 33/225; G01N 21/314; G01N 21/31; G01N 33/004; G01N 33/0057; G01N 2021/1795; G01J 3/42; G01J 3/443
USPC ...................................... 250/222.2, 221, 576
See application file for complete search history.

(56) References Cited

U.S. PATENT DOCUMENTS 7,352,463 B2 *    4/2008    Bounaix ............. G01N 21/031
                                                     356/437

* cited by examiner

*Primary Examiner* — Que T Le
(74) *Attorney, Agent, or Firm* — Barry Choobin; Patent 360

(57) ABSTRACT

A system and method to accurately estimate the strength and changes of the monitoring signal for sensing applications, this invention involves the monitoring of signal strength and changes through the use of a pseudorandom binary sequence bit stream to modulate the transmitter of a data link, when beating the transmitter signal with absorption structure signal from the sensor at the receiver, the changes in the received signal strength are proportional to the sensing signal being monitored. The received signal bit pattern is monitored by an error detector scheme to report a Bit Error Rate level based on the changes in the sensing signal level as compared to the bit stream from the transmitter. This results in a very accurate robust monitoring technique with high consistency and repeatability.

14 Claims, 4 Drawing Sheets

SYSTEM AND METHOD OF DETECTING ATMOSTPHERIC TRACE GAS CONCENTRATIONS IN A CELL

FIELD OF INVENTION

The present invention generally relates to a tunable laser and in particular to a system and method for detecting trace gas concentration in the atmosphere.

BACKGROUND

Earlier days, a cell containing a gas was used to analyze the molecular structure of many gases by transmitting electromagnetic waves of predetermined frequencies and detecting the reduction in the intensity of the electromagnetic waves at discrete frequencies after passage there through. The extent of microwave absorption by a gas at a particular frequency is designated as an absorption line. Each of the gas concentration has a unique set of absorption lines differing from that of any other gas, and the absorption lines being invariant to external factors such as time, pressure and temperature.

Besides using microwaves, RF waves or other waves are used to detect trace gases. Instruments are used to measure carbon cycle gases in the atmospheric column which need comparable ground validation measurements. Currently, measuring carbon dioxide ($CO_2$) and methane ($CH_4$) in the atmospheric column is by a network which is based on ground-based Fourier Transform Spectrometers that record direct solar spectra in the near-infrared spectral region. For the spectra, accurate and precise column-averaged abundance of $CO_2$, $CO$, $C_2H_2$ and $CH_4$ are retrieved. Some globally distributed sensing network can also be used to trace gas concentration.

In the fields of metrology and sensing applications, lasers are used to provide a source for optical signals and to process at various wavelengths. Sensing applications use tunable lasers to monitor absorption peaks in gases or liquids in order to identify these elements and to measure their concentrations. Laser heterodyne radiometry is a technique for detecting absorption signals that was adapted from radio receiver technology and optical communication. In a radio receiver, a weak input signal from a radio antenna is mixed with a stronger local oscillator signal. Since the early nineteen seventies, laser heterodyne radiometry (LHR) has been used for atmospheric studies. The beat signal of the absorption region and the local oscillator is detected with an optical receiver and then the RF signal is amplified using a set of video signal amplifiers, bias-tee, filters, and a chain of amplifiers. The quality of the recovered signal is greatly dependent on the noise performance of the amplifier chain that produce unpredictable results that suffer from repeatability of the magnitude of the signal changes, specifically for small signal changes that are impossible to monitor with such technique. In addition to those issues, demand frequent calibration cycles and changes in the ambient temperature affects the RF amplifier response.

The tunable diode laser absorption spectroscopy in a process industry became one of the most promising techniques for online trace gas analyzing. Restricted by its principle, the measurement result of tunable diode laser absorption spectroscopy system is seriously affected by temperature and gas pressure variation. For this reason, most tunable diode laser absorption spectroscopy systems employ temperature and pressure sensors, which can provide information for partly correcting the error.

Prior art systems use analysis system which comprises an optical module, a fluid module, an electrical module, and a mechanical packaging module to trace gas which is complex, high cost, and less reliable.

Hence, there exists a need in the art for a method and system comprising a tunable laser with pseudorandom Binary sequence generator to accurately estimate the strength and changes of the monitoring signal for a sensing application.

SUMMARY

The objective of the invention is to provide an improved tunable laser trace gas analyzer, which determines the concentration of a trace gas.

The system and method are disclosed for detecting trace gas concentration using tunable laser. The trace gas can comprise of ozone $O_3$, sulfur dioxide $SO_2$ and nitrogen oxides $NO_x$, carbon dioxide $CO_2$ and methane $CH_4$, carbon monoxide $CO$ and acetylene $C_2H_2$, and other greenhouse gases.

Accordingly, a first embodiment of the present invention relates to a method for detecting trace gas concentration in the atmosphere. In one embodiment, the method includes transmitting a laser beam using a tunable laser and attenuating the light wave from the tunable laser at the wavelength for the monitored gas absorption peak resulting in lower optical power in optical waveguides using an absorption cell. Further, the method modulates the signal from the absorption cell using a Pseudo Random Binary Sequence generated by a Pulse Pattern Generator and transmits a degraded signal to the receiver. Further, the method introduces an electrical signal to optimize the decision threshold circuit using a signal generator, and optimizes the BER performance for the baseline BER reading. Further, the method proves the RF connection to the error detector from the decision threshold circuit and measures the Bit error rate (BER) and the Bit error rate (BER) value using error detector and the difference value corresponds to the signal strength at the input of the receiver.

According to one implementation of the present invention, the system comprises a tunable laser operating in a continuous fashion with a small emission bandwidth; other tunable laser such as a Q-switched and mode-locked lasers can also operate at a tuned wavelength. In the preferred embodiment, the tunable laser emits laser beam which passes to the absorption cell and the attenuated signal from the absorption cell is transmitted to the modulator where the signal gets modulated by pseudo random binary sequence generated by the pulse pattern generator. Further, the receiver receives the transmitting signal which is beated by the absorption structure signal from the sensor. The signal generator provides an electrical signal to optimize the decision threshold circuit, to optimize the BER performance for the baseline BER reading and the output of the decision threshold block provides the RF connection, to the error detector. The received signal bit pattern is monitored by an error detector scheme to report Bit Error Rate level based on the changes in the sensing signal level as compared to the bit stream from the transmitter.

In another embodiment, the method is used for detecting green house gas concentration in an atmosphere. In one embodiment, the method comprises a monitoring system using remote atmospheric light collimator that collects data and injects it through an optical fiber to the input of the modulator, wherein the optical fiber is positioned between the laser and the modulator, with the signal out of the receiver being characterized by an error detector to monitor the BER based on the pattern that is injected into the modulator.

According to one embodiment of the present invention the monitoring system using remote atmospheric light collimator that collects data and injects it through an optical fiber to the output of the modulator, wherein the optical fiber is positioned between the modulator and the receiver, with the signal out of the receiver being characterized by an error detector to monitor the BER based on the pattern that is injected into the modulator.

The foregoing and other features of the present invention will be more readily apparent from the following detailed description and drawings of an illustrative embodiment of the invention.

BRIEF DESCRIPTIONS OF SEVERAL VIEWS OF DRAWINGS

FIGURES

Reference Numerals

Figure 1:
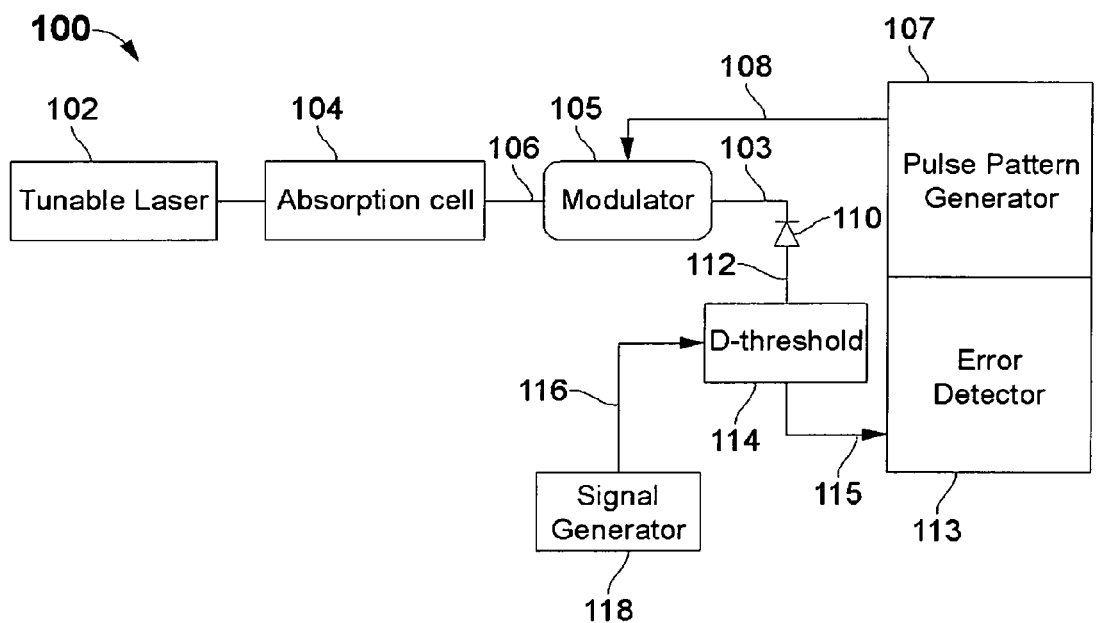
FIG. 1 illustrates a block diagram of one embodiment of a system incorporating aspects of the present invention.

100—System for monitoring gas concentration
102—Tunable laser to provide laser signal
104—Absorption cell to attenuate light waves
105—Modulator to modulate the input signal
103, 106—Optical waveguide to propagate light waves
107—Pulse Pattern Generator to generate the pulse patterns
108—Pseudo random bit sequence
110—Receiver to receive the modulated signal
112—Degraded signal/attenuated signal from the transmitter
113—Error detector to generate bit error rate (BER)
114—Decision threshold circuit for optimization
116—Electrical Signal power to the decision threshold circuit
115—RF connection to transfer signal to error detector
118—Signal generator to generate electrical signal
211—Remote collimator apparatus to collect data from the atmosphere/sensing signal
214—Optical fiber cable to transmit the signal
206—Optical combiner to provide the signal as input to the modulator
306—Optical combiner to provide the signal as output to the modulator

DETAILED DESCRIPTION OF DIFFERENT EMBODIMENTS

The present invention is related to system and method to accurately estimate the strength and changes of the monitoring signal for sensing applications. Tunable laser trace gas analyzer is used to determine the concentration of a trace gas. The laser emits a laser beam at a spatial frequency of a wave, either in cycles per unit distance or radians per unit distance, which is variable in response to the amplitude.

The present invention relates to a system and method for detection of a trace gas utilizing the tunable laser. The laser light source radiating in a narrowband of the infrared range of the electromagnetic spectrum, where the trace gas detection system is configured for detection of optical spectra at wavelengths in the wavelength range (for methane detection can be tuned between about 3.2 micrometer to about 3.5 micrometer wavelength range). The method includes providing a large dynamic range for reporting changes in absorption peak strength and the tunable laser exhibiting high detection sensitivity in the presence of mechanical disturbances and temperature variations.

In the embodiments described herein, the trace gases include CO2, C2H2, CH4 and CO. The measurements of CO2, CH4 and CO, C2H2 are in the range of approximately 1.5 to 1.6 microns. These wavelengths are much shorter than the normal wavelengths. The weak input signal which has undergone absorption by a trace gas is referred to as a greenhouse gas.

In an embodiment, according to the present invention, the system 100 comprises of tunable laser 102 for emitting tunable wavelength. An absorption cell 104 for attenuating the laser light from the tunable laser 102. A plurality of Optical waveguides 103 and 106 for guiding the light during the data transmission. A modulator 105 for modulating the signal using pseudorandom bit sequence 108 from the pattern generator 107. The receiver 110 receives the signal from the modulator 105. The receiver 110 transmits the degraded signal 112 to a decision threshold circuit 114. The Signal generator 118 sends an electrical signal 116 to the decision threshold circuit 114. The Decision threshold circuit 114 sends RF signal 115 to the error detector 133 for bit error optimization. This disclosure concerns about a method and system to accurately estimate the strength and changes of the monitoring signal for sensing applications.

FIG. 1 is a block diagram illustrating a tunable laser 102 for detecting a trace gas such as green house gas configured to receive an input signal from an optical system for reference, which in one embodiment includes a remote atmospheric light collimator system. The optical system is generally configured to collect signal, which can be green house gas that includes an absorption signal of a trace gas. The optical system can include, or be coupled to any system that is used to point the collection optics to track the atmosphere throughout the day.

Changes in the concentration of the trace gas can be realized by analyzing changes in the input signal by supplying the input signal to the trace gas concentration and providing that information in a suitable format. According to an embodiment, as illustrated in FIG. 1, relates to a system 100 for detecting trace gas concentration. Here the tunable laser 102 emits wavelength at a tunable frequency. The output from the tunable laser 102 is transmitted to the absorption cell 104 and the absorption cell 104 attenuates the light wave from the tunable laser 102 at the wavelength for the monitored gas absorption peak, resulting in a lower optical power. Two optical waveguides 103 and 106 can be used which are spatially inhomogeneous structure for a guiding light. These two optical waveguides 103 and 106 are positioned before and after a modulator 105. Optical waveguides 103 and 106 can be used for efficient data transmission in the form of light pulses. In this embodiment, laser wavelength after passing through the absorption cell 104, may be modulated by a pseudorandom binary sequence 108 generated by a pulse pattern generator 107. The pseudorandom binary sequence 108 bit can modulate the signal for broad frequency content characterization of link and generates bit error rate reference. The pseudorandom binary sequence (PRBS) 108 duty cycles resemble the duty cycle of a continuous signal and its maximum duty cycle is ½. The pulse pattern generator 107 in some examples can have shift register of length n equal to the order of polynomial and modulo 2 (binary adder). The Period p of the pseudorandom binary sequence 108 depends on the shift register length (n). If the period of pseudorandom binary sequence 108 needs to be longer then the shifter register length should be longer. The laser attenuated wavelength is modulated by the pseudorandom binary sequence 108 from the pulse pattern generator 107, which occurs in the modulator 105, and the modulated data link is sent to the receiver 110. As the transmission signal gets attenuated, the received signal will be degraded in strength in the receiver 110. Beating the transmitter signal with the absorption structure signal from the sensor at the receiver 110 create changes in the received signal strength, which is proportional to the sensing signal being monitored.

Further, the degraded signal 112 is transmitted to the decision threshold circuit 114 and the signal generator 118 provides an electrical signal 116 to the decision threshold circuit 114 to optimize the decision. Further, the signal from the decision threshold circuit 114 is transmitted to the error detector 113. The output of the decision threshold block provides the RF connection 115 to the error detector 113 and the Bit Error rate testing can be used to characterize the signal strength and monitor variation. The received signal bit pattern is monitored by an error detector 113 having a scheme to report Bit Error Rate level based on the changes in the sensing signal level as compared to the bit stream from the transmitter. Bit Error Rate (BER) value is generated that corresponds to the signal strength at the input of the receiver 110. This BER value is compared to the baseline BER before injecting any gas to the absorption cell 104, and the resulting difference in BER performance correspond to the absorption strength of the gas in the cell. Decision threshold circuit 114 optimizes the BER performance for the baseline BER reading. Further, the degradation in the BER due to absorption may be compared against the baseline BER, to extract the gas concentration. This method provides a large dynamic range for reporting changes in absorption peak strength.

In this embodiment the monitoring system 100 uses an absorption cell 104 between tunable laser 102 and the modulator 105, with the signal out of a receiver 110 being characterized by an error detector 113 to monitor the BER based on the pattern that is injected into the modulator 105. The tunable laser 102 may further include an external cavity configured to provide low spectral line width for accurate absorption line measurement. The external cavity design also provides low relative intensity noise performance to improve accuracy of monitoring results. By tuning the laser 102 to the required gas signature wavelength, different gases may be characterized (which can also be automated). The wavelength depends on the gas to be characterized and the tunable laser 102 can sweep between different gas absorption peaks and also can provide multiple readings concurrently. This method improves a testing dynamic range by orders of magnitude in monitoring the bit error rate.

Figure 2:
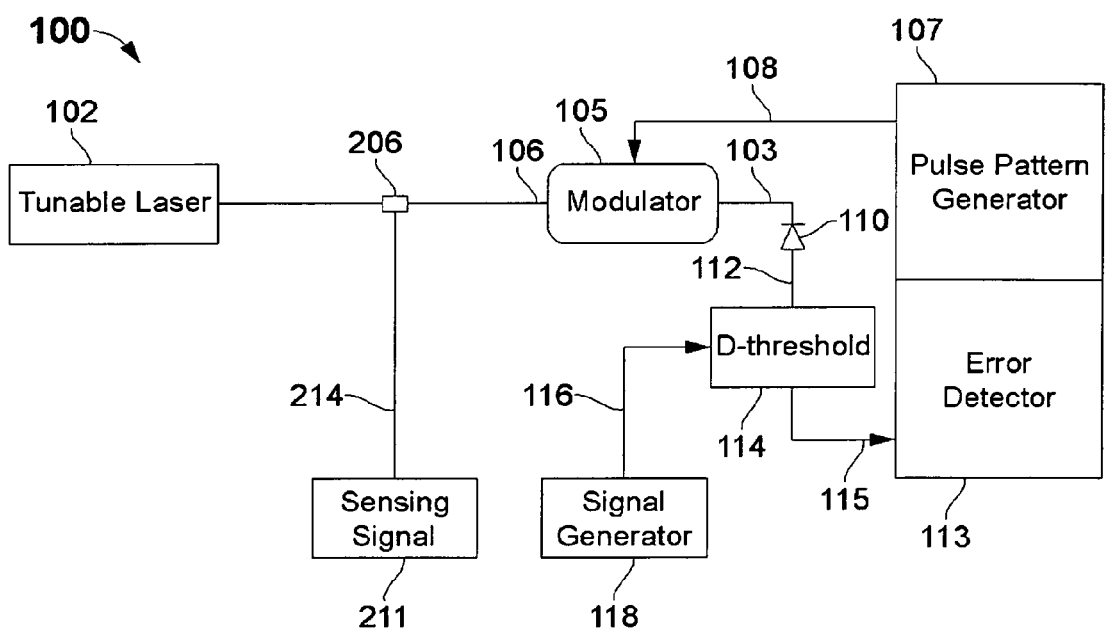
FIG. 2 illustrates a block diagram of an embodiment of a system incorporating aspects of the present invention.

In some embodiments, as depicted in FIG. 2 shows the monitoring system in which the signal being characterized comes from a remote collimator of light that is monitoring atmospheric gases which provide the sensing signal 211. The remote collimator apparatus is connected to the monitoring system with a fiber cable 214 that is combined with the tunable laser output 102 using an optical combiner 206. The Optical combiner 206 can be used to combine the delayed pulses and then form the desired code sequence before sending the signal into the modulator 105. The remote atmospheric light collimator that collects data and injects it to the input of the modulator 105, which is present between tunable laser 102 and modulator 105 through an optical fiber 214. The modulator 105, can modulate the signal using pseudorandom binary sequence 108 generated by a pulse pattern generator 107. The Optical waveguide 103 is located after modulator 105 which propagates the input signal along a direction of propagation of the light. The pseudorandom binary sequence bit stream modulates the transmitter of a data link which is directed from the tunable laser 102 beating the transmitter signal with an absorption structure signal from the sensor at the receiver 110, to create changes in the received signal strength which is proportional to the sensing signal being monitored. The received signal can be a degraded signal since data loss occurs during the transmission of the signal from the transmitter to the receiver 110. The received signal bit pattern is monitored by an error detector 113 and the degraded signal 112 can be transmitted from the receiver 110 to the decision threshold circuit for further optimization. The Signal generator 118 provides an electrical signal 116 to optimize the decision threshold circuit 114 which in turn optimize the BER performance for the baseline BER reading. The output of the decision threshold block provides the RF connection 115, to the error detector 113.

The transmitted pseudorandom bit sequence is compared with the bit sequence received at the error detector 113 and the Bit Error Rate (BER) value is generated that corresponds to the signal strength at the input of the receiver 110. Further, the Error detector BER is compared to the baseline BER before injecting any signal from the sensing fiber 214, and the resulting difference in the BER performance correspond to the absorption strength of the gas in the cell. The degradation in the BER is due to the absorption signal compared against the baseline BER, to extract the gas concentration. By tuning the tunable laser 102 to the required gas signature wavelength, different gases may be characterized (which can also be automated).

For example, the functionality described above with respect to the monitoring system can be implemented to trace or characterize the greenhouse gas but not limited to CO2, CO, C2H2 and CH4. When large measurement accuracy is desired, as may be the case, for example, when using the tunable laser 102 to measure concentration variations in atmosphere where the changes in trace gas concentration is high. The processor may instruct the modulator 105 to modulate the signal from the laser, or to turn off modulation, depending on the tunable laser 102 operating under the modulation schemes. In an embodiment, other alternate modes such as direct absorption mode can be used.

Figure 3:
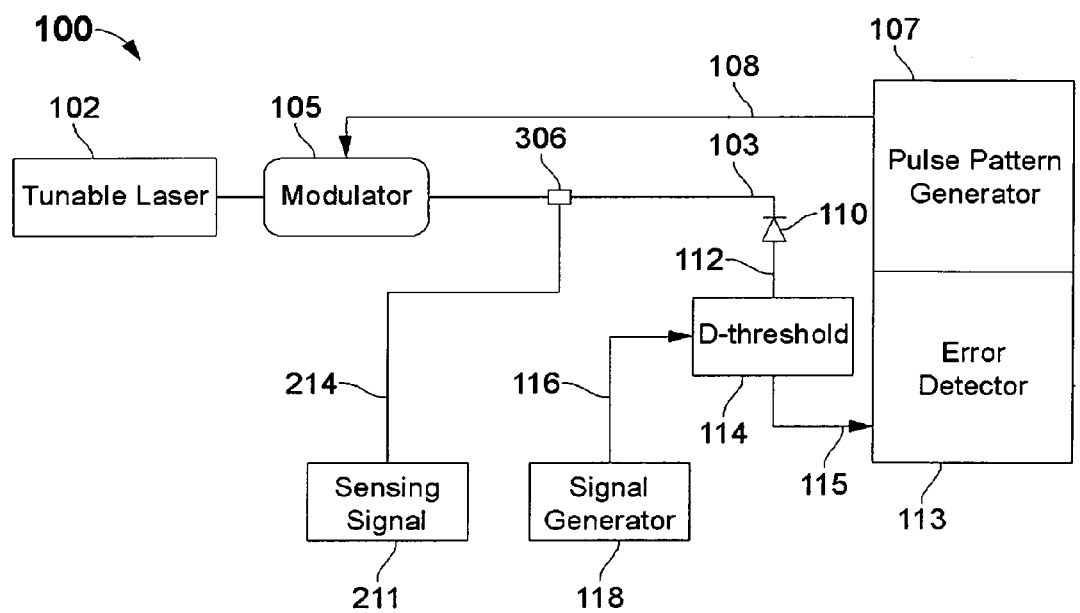
FIG. 3 illustrates a block diagram of an embodiment of a system incorporating aspects of the present invention.

According to another embodiment FIG. 3 describes system 100 incorporating aspects of the present invention is illustrated. In this embodiment, the monitoring system comprises of a tunable laser 102 and other components such as a modulator 105, an error detector 113, and so on. Further, the Remote atmospheric light collimator can be connected to the tunable laser 102 at different positions. In an embodiment, the signal being characterized is received from the remote collimator of light that is monitoring the atmospheric gas which provides the sensing signal 211. The remote atmospheric light collimator is configured to collect data and inject it through an optical fiber 214 to the output of a modulator 105. Further, the apparatus is connected to the monitoring system with a fiber cable 214 that is combined with the modulator output, using an optical combiner 306. The apparatus can be located between the modulator 105 and the receiver 110 and the absorption signal from the tunable laser 102 is modulated with the modulator 105 and introduced into the optical waveguide 103. Further, the signal pattern (that is) pseudorandom binary sequence 108 from the pattern generator 107, which in this example is PRBS 108 is supported with multiple shift registers. Further, the absorbed light signal from the modulator 105 is transmitted to the receiver 110 and the receiver is configured to beats the transmitter signal with an absorption structure signal received from the sensor configured in the receiver. Further, the signal monitored at the receiver 110 is transmitted to the decision threshold circuit 114 and the received signal bit pattern is monitored by an error detector 113. Further, the signal generator 118 is configured to provide an electrical signal 116 to optimize the decision threshold circuit 114 and optimize the BER performance for the baseline BER reading. Further, the output signal of the decision threshold block provides the RF connection 115 to guide the output signal to the error detector 113. Further, the pseudorandom bit sequence 108 is compared with the bit sequence received at the error detector 113 and the Bit Error Rate (BER) value is generated that corresponds to the signal strength received at the input of the receiver 110. Further, the generated BER value is compared to the baseline BER before injecting any signal from the sensing fiber 214, and the resulting difference in the BER performance correspond to the absorption strength of the gas in the cell. In an embodiment, the degradation in BER due to the absorption can be compared against the baseline BER, to extract the gas concentration. By tuning the laser 102 to the required gas signature wavelength, different gases may be characterized (which can also be automated). Further, when the bit error rate level is reported based on the changes in the sensing signal level as compared to the bit stream from the transmitter, the robust monitoring technique can depict a result, which is considered to be accurate with high consistency and repeatability.

In an embodiment, the modulator 105 can operate in a radio frequency but not limited other electromagnetic frequencies. The decision threshold circuit 114 and the error detector 113 are not limited in scope by the specific embodiments described herein. Indeed, other various embodiments of and modifications to the present invention, in addition to those described herein, will be apparent to those of ordinary skill in the art from the foregoing description and accompanying drawings.

Figure 4:
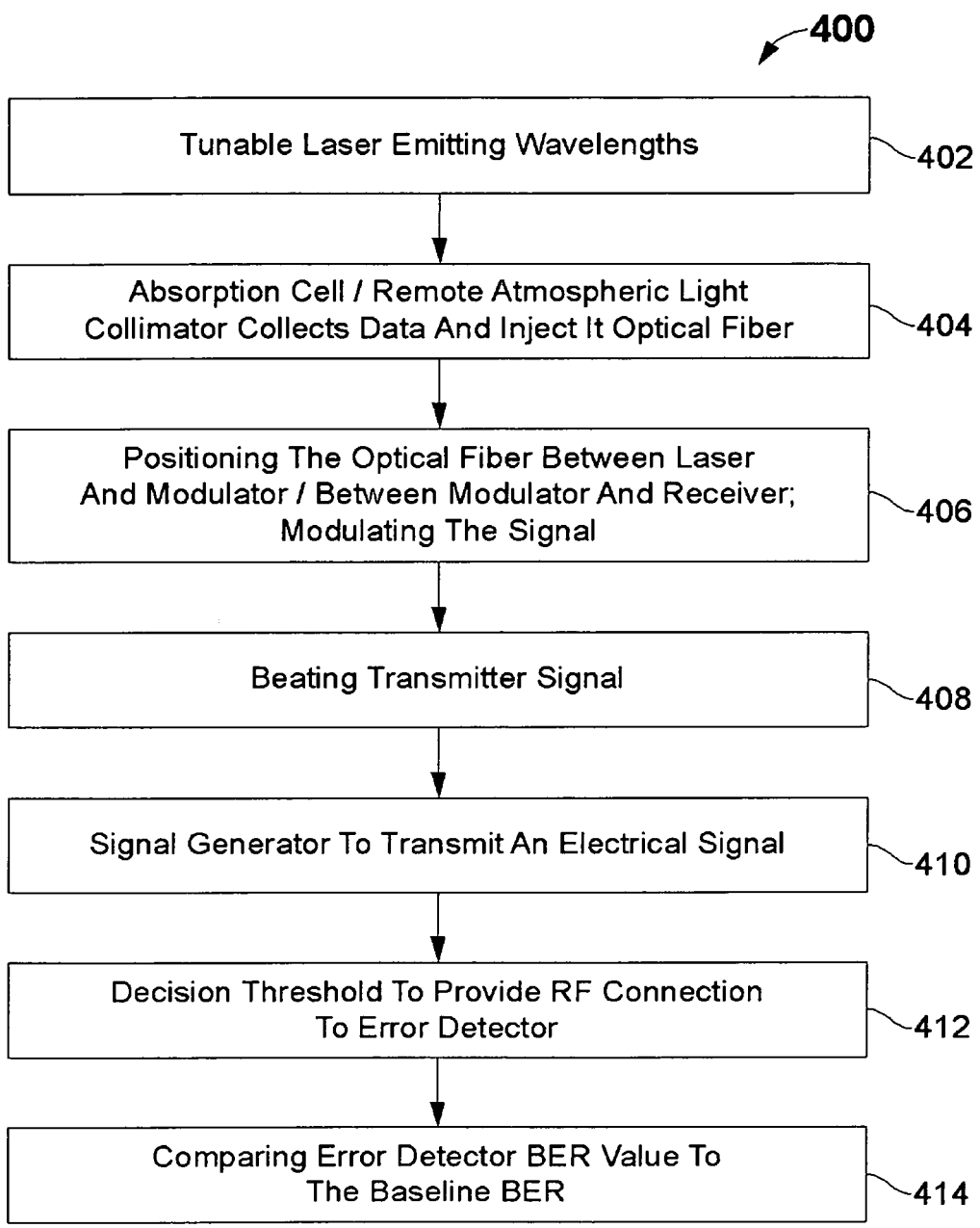
FIG. 4 illustrates a flow chart of one embodiment of a process incorporating aspects of the present invention.

According to an embodiment of the present invention FIG. 4 is a flow diagram illustrating the process or method 400 for measuring a concentration of a trace gas concentration with high resolution including: at step 402, the system 100 is configured to provide a tunable laser 102 to emit wavelengths at a tuned frequency; at step 404, the system 100 is configured to utilize the absorption cell 104 for attenuating the light wave from the tunable laser 102 at certain wavelength and transmits the signal to a modulator and other alternative process using a remote atmospheric light collimator that collects data and injects the data through an optical fiber 214. At step 406 the system 100 positions the optical fiber 214 between the tunable laser 102 and the modulator 105 or between the modulator 105 and the receiver 110 to modulate the signal by the pseudorandom binary sequence 108 by the pattern generator 107. Further, at step 408, the system 100 is configured to beat the transmitter signal with the absorption structure signal received from the sensor at the receiver 110. Further, at step 410, the system 100 is configured with a signal generator 118 to transmit an electrical signal 117 to optimize a decision threshold circuit 114. Further, at step 412, the system 100 is configured with the decision threshold 114 to provide an RF connection 115 to the error detector 113. Further, at step 412, the system 100 is configured with an error detector 113 to receive the signal bit pattern, using an error detector 113 scheme to report a bit error rate level, that is determined based on the changes in the sensing signal. Further, at step 414, the system 100 is configured to compare the error detector BER value to the baseline BER and the resulting difference in BER performance correspond to the absorption strength of the gas in the cell.

The aspects of the disclosed various embodiments of this invention relates to measuring trace of green house gases in the atmosphere using tunable laser monitoring system. Disclosed method can be used to accurately estimate the strength and changes of the monitoring signal for sensing applications, this invention involves the monitoring of signal strength in the fields of not limited to metrology and sensing applications.

Thus, such other embodiments and modifications are intended to fall within the scope of the present invention. Further, although the present invention has been described herein in the context of a particular implementation in a particular environment for a particular purpose, those of ordinary skill in the art will recognize that its usefulness is not limited thereto and that the present invention may be beneficially implemented in any number of environments for any number of purposes. Accordingly, the claims set forth below should be construed in view of the full breadth and spirit of the present invention as described herein.

What is claimed is:

1. A method for detecting atmospheric trace gas concentrations with high resolution, wherein the method comprises of:

emitting by a tunable laser, a laser beam at a tuned frequency;

transmitting the laser beam to a modulator;

injecting a sensing signal through an optical fiber, wherein the sensing signal is collection of atmospheric data;

combining the sensing signal with a first signal from the modulator with an optical combiner, wherein the first signal is the output from the modulator generated by using the laser beam;

receiving at an optical waveguide, a second signal, wherein a second signal is generated combining the sensing signal with a first signal from the modulator;

generating a pseudorandom binary sequence with a pulse pattern generator;

modulating the laser beam by the modulator, with the pseudorandom binary sequence;

monitoring the second signal by a receiver, wherein the receiver beats the second signal with an absorption structure signal received from at least one sensor configured in the receiver;

receiving by a decision threshold circuit, at least one output from the receiver;

emitting an electrical signal by a signal generator to the decision threshold circuit, for optimization of the output signal and to provide an RF connection to an error detector;

receiving by the error detector, an output signal bit sequence generated from the decision threshold circuit;

comparing by the error detector, an input and the output bit sequence for generating a Bit Error Rate (BER) value that corresponds to a signal strength received at the input of the receiver; and comparing a baseline BER corresponds to the input signal with the BER value corresponds to the output signal bit sequence generated from the decision threshold circuit received from the error detector, difference between the baseline BER and the BER value received from the error detector being absorption strength of a gas in a cell.

2. The method of claim 1, wherein the pulse pattern generator generates the pseudorandom binary sequence bit and modulates the laser beam.

3. The method of claim 2, wherein the pulse pattern generator provides characterization of trace gas and generates a bit error rate reference.

4. The method of claim 1, wherein an error detector BER (bit error rate) testing characterizes the signal strength and monitors a signal strength variation.

5. The method of claim 4, wherein the error detector BER (bit error rate) testing improves dynamic range by orders of magnitude in monitoring the bit error rate.

6. The method of claim 1, wherein trace gas comprises the following elements: carbon dioxide (CO2), methane (CH4), carbon monoxide (CO), Acetylene (C2H2), and other greenhouse gas.

7. A system for detecting trace gas concentration with high resolution, wherein the system comprising:
 a tunable laser configured to emit a laser beam at a tuned frequency;
 a modulator, configured to be transmitted with the laser;
 an optical fiber configured to receive injection of a sensing signal,
 wherein the sensing signal is collection of atmospheric data;
 an optical combiner configured to combine the sensing signal with a first signal from the modulator,
 wherein the first signal is the output from the modulator generated by using the laser beam;
 an optical waveguide, configured to receive a second signal,
 wherein a second signal is generated combining the sensing signal with a first signal from the modulator;
 a plus pattern generator configured to generate a pseudorandom binary sequence;
 the modulator further configured to:
  modulate the laser beam by the modulator, with the pseudorandom binary sequence;
 a receiver configured to monitor the second signal,
 wherein the receiver beats the second signal with an absorption structure signal received from at least one sensor configured in the receiver;
 a decision threshold circuit configured to receive at least one output from the receiver;
 a signal generator to emit an electrical signal to the decision threshold circuit for optimization of the output signal and to provide an RF connection to an error detector; and
 the error detector configured to:
  receive an output signal bit sequence generated from the decision threshold circuit,
  compare an input and the output bit sequence for generating a Bit Error Rate (BER) value that corresponds to a signal strength received at the input of the receiver, and
  compare a baseline BER corresponds to the input signal with the BER value corresponds to the output signal bit sequence generated from the decision threshold circuit received from the error detector, difference between the baseline BER and the BER value received from the error detector being absorption strength of a gas in a cell.

8. The system of claim 7, further comprising the step of changing the laser frequency is achieved by tuning an external cavity to provide a low relative intensity noise, a low spectral line width, and to yield accurate absorption line measurement.

9. The system of claim 7, wherein the tunable laser is configured to sweep between different gas absorption peaks to provide multiple readings concurrently.

10. The system of claim 7, wherein the pulse pattern generator generates the pseudorandom binary sequence.

11. The system of claim 7, wherein the gas comprises of the following elements: carbon dioxide (CO2), methane (CH4) and carbon monoxide (CO), and other green house gas.

12. The system of claim 7, wherein the signal generator is configured to provide an electrical signal to optimize the decision threshold circuit.

13. The system of claim 12, wherein the decision threshold circuit configured to provide RF connection to the error detector.

14. The method of claim 1, wherein the sensing signal is collected by using a remote atmospheric light collimator.

* * * * *